(12) United States Patent
Mortz

(10) Patent No.: US 6,987,994 B1
(45) Date of Patent: Jan. 17, 2006

(54) PULSE OXIMETRY SPO2 DETERMINATION

(75) Inventor: Margaret S. Mortz, Lafayette, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/700,319

(22) Filed: Nov. 3, 2003

Related U.S. Application Data

(63) Continuation of application No. 09/963,219, filed on Sep. 25, 2001, now Pat. No. 6,714,803, which is a continuation of application No. 09/370,962, filed on Aug. 10, 1999, now Pat. No. 6,385,471, which is a continuation of application No. 08/405,569, filed on Mar. 16, 1995, now Pat. No. 5,934,277, which is a continuation of application No. 07/753,761, filed on Sep. 3, 1991, now abandoned.

(51) Int. Cl.
*A61B 5/00* (2006.01)

(52) U.S. Cl. .................................. 600/336

(58) Field of Classification Search ........... 600/310, 600/322, 323, 330, 331, 336
See application file for complete search history.

(56) References Cited

U.S. PATENT DOCUMENTS

| | | | |
|---|---|---|---|
| 4,167,331 A | 9/1979 | Nielsen | |
| 4,266,554 A | 5/1981 | Hamaguri | |
| 4,586,513 A | 5/1986 | Hamaguri | |
| 4,623,248 A | 11/1986 | Sperinde | |
| 4,651,741 A | 3/1987 | Passafaro | 600/328 |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,784,150 A | 11/1988 | Voorhies et al. | |
| 4,796,636 A | 1/1989 | Branstetter et al. | |
| 4,802,486 A | 2/1989 | Goodman et al. | |
| 4,805,623 A | 2/1989 | Jobsis | |
| 4,807,631 A | 2/1989 | Hersh et al. | |
| 4,819,752 A | 4/1989 | Zelin | |
| 4,822,568 A | 4/1989 | Tomita | |
| 4,824,242 A | 4/1989 | Frick et al. | |
| 4,863,265 A * | 9/1989 | Flower et al. | 600/322 |
| 4,869,253 A | 9/1989 | Craig, Jr. et al. | |
| 4,869,254 A | 9/1989 | Stone et al. | |
| 4,883,353 A | 11/1989 | Hausman et al. | |
| 4,911,167 A | 3/1990 | Corenman et al. | |

(Continued)

*Primary Examiner*—Eric F. Winakur
(74) *Attorney, Agent, or Firm*—Marsh Fischmann & Breyfogle LLP

(57) ABSTRACT

The improved pulse oximeter preprocesses the sets of red and infrared signals received from the probe to remove ambient light, to remove noise, and to de-exponeniate the signals. The linearity of the processed red and infrared signals allows the use of statistical techniques such as linear regression and linear correlation to fit a best fit straight line to the set of pairs of processed red and infrared data points and to measure the goodness of the straight line fit to these data points. The result of this analysis is a linear regression slope and a goodness of fit correlation coefficient. The correlation coefficient is a measure of the linearity of the input data points and, if less than a predetermined threshold, it indicates that a distorted signal has been received from the probe. This permits the pulse oximeter to detect probe off conditions and/or motion in the patient. The computed linear regression slope is converted to a RRatio which is used in a empirical calibration formula to compute the average SpO2 value. The minimum size of the data set required for high confidence calculations using this apparatus is significantly smaller than the a pulse period and permits faster response to changing input data.

43 Claims, 5 Drawing Sheets

U.S. PATENT DOCUMENTS

| | | |
|---|---|---|
| 4,928,692 A | 5/1990 | Goodman et al. |
| 4,948,824 A | 8/1990 | Auerbach |
| 4,955,379 A | 9/1990 | Hall |
| 5,028,787 A | 7/1991 | Rosenthal et al. |
| 5,048,524 A | 9/1991 | Bailey |
| 5,119,815 A | 6/1992 | Chance |
| 5,219,400 A | 6/1993 | Jacot et al. |
| 5,259,381 A | 11/1993 | Cheung et al. |
| 5,351,685 A | 10/1994 | Potratz |
| 5,379,238 A | 1/1995 | Stark |
| 5,482,036 A * | 1/1996 | Diab et al. .................. 600/364 |
| 5,503,148 A | 4/1996 | Pologe et al. |
| 5,934,277 A * | 8/1999 | Mortz ........................ 600/323 |
| 6,157,850 A | 12/2000 | Diab et al. .................. 600/323 |
| 6,263,222 B1 | 7/2001 | Diab et al. .................. 600/310 |
| 6,385,471 B1 * | 5/2002 | Mortz ........................ 600/323 |
| 6,501,975 B2 * | 12/2002 | Diab et al. .................. 600/336 |
| 6,714,803 B1 * | 3/2004 | Mortz ........................ 600/323 |

* cited by examiner

PULSE OXIMETRY SPO2 DETERMINATION

RELATED APPLICATIONS

This patent application is a continuation of U.S. patent application Ser. No. 09/963,219 entitled PULSE OXIMETRY $SpO_2$ DETERMINATION, which was filed on Sep. 25, 2001, and issued on March 30, 2004 as U.S. Pat. No. 6,714,803, which is a continuation of U.S. patent application Ser. No. 09/370,962 entitled SYSTEM FOR PULSE OXIMETRY $SpO_2$ DETERMINATION, which was filed on Aug. 10, 1999, and issued on May 7, 2002 as U.S. Pat. No. 6,385,471, which is a continuation of U.S. patent application Ser. No. 08/405,569 entitled IMPROVED SYSTEM FOR PULSE OXIMETRY $SpO_2$ DETERMINATION, which was filed on Mar. 16, 1995, and issued on Aug. 10, 1999 as U.S. Pat. No. 5,934,277, which is a continuation of U.S. patent application Ser. No. 07/753,761 entitled PULSE OXIMETRY $SpO_2$ DETERMINATION, which was filed on Sep. 3, 1991, now abandoned. The entire disclosures of U.S. patent application Ser. Nos. 09/963,219, 09/370,962, 08/405,569 and 07/753,761 are incorporated herein by reference.

FIELD OF THE INVENTION

This invention relates to pulse oximeters which noninvasively measure the oxygen saturation of hemoglobin in arterial blood and, in particular, to an improved system for performing these calculations and for discriminating valid signals from invalid data such as caused by probe-off conditions or motion artifacts.

Problem

It is a problem in the field of pulse oximeters to accurately measure the oxygen saturation of the hemoglobin in arterial blood without having a significant error content due to ambient noise. It is also a problem to determine when the probe used to perform the measurement is producing data with a noise component that is too large to provide an oxygen saturation reading of sufficient accuracy. The oxygen saturation (SpO2) of the hemoglobin in arterial blood is determined by the relative proportions of oxygenated hemoglobin and reduced hemoglobin in the arterial blood. A pulse oximeter calculates the SpO2 by measuring the difference in the absorption spectra of these two forms of hemoglobin. Reduced hemoglobin absorbs more light in the red band than does oxyhemoglobin while oxyhemoglobin absorbs more light in the infrared band than does reduced hemoglobin. The pulse oximeter includes a probe that is placed in contact with the skin, in a vascularized tissue region, either-on a flat surface in the case of reflectance probes or across some appendage in the transmission case. The probe contains two light emitting diodes (LEDs), each of which emits light at a specific wavelength, one in the red band and one in the infrared band. The amount of light received after interacting with the tissue adjacent to the LEDs is measured many times a second at both wavelengths.

The tissue contains arterial, capillary and venous blood as well as muscle, connective tissue and bone. Therefore the red and infrared signals received from the probe contain a non-pulsatile component which is influenced by the absorbency of tissue, venous blood, capillary blood, non-pulsatile arterial blood, the intensity of the light source and the sensitivity of the detector. The pulsatile component of the received signals is an indication of the expansion of the arteriolar bed with arterial blood. The amplitude of the pulsatile component is a very small percentage of the total signal amplitude and depends on the blood volume change per pulse and the SpO2. The received red and infrared signals have an exponential relationship to their respective incident intensities. Therefore, the argument of the received red and infrared signals have a linear relationship and these received signals can be filtered and mathematically processed using either derivatives or logarithms. The effects of different tissue thicknesses and skin pigmentation can be removed from the received signals by normalizing the processed signal by a term that is proportional to the non-pulsatile portion of the received signal intensity. Taking the ratio of the mathematically processed and normalized red and infrared signals results in a number which is theoretically a function of only the concentration of oxyhemoglobin and reduced hemoglobin in the arterial blood, provided that the concentration of dyshemoglobins in the arterial blood is sufficiently small.

This data is significantly impacted by the presence of noise, which is manifested in many forms. Any phenomena, whether mechanical or electrical or optical, that causes an artifact in the pulsatile component of the received signals compromises instrument performance. An example is that any transient change in the distance between the light emitting diodes and the detector can result in an error signal at both wavelengths. These pulse sources can course annoying false positive alarms which are of concern in a critical care setting because instruments with frequent alarms are often ignored or the alarms are disabled. Motion artifacts can be caused by patient movement and frequently mimic vascular beats with frequencies well within normal physiological ranges. A second source of noise is the introduction of ambient light into the probe. Any light incident on the detector and not originating from the light emitting diodes is considered noise. Many of these noise sources are not easily filtered out of the resultant signal and represent a significant error component in existing pulse oximeters.

Solution

The above-described problems are solved and a technical advance achieved in the field by the improved system for noninvasively calculating the oxygenation of hemoglobin in arterial blood using a pulse oximeter. This improved system takes advantage of the basic statistical property of pulse oximetry signals that the measured blood oxygen saturation appears as a constant over a small set of measurements. Properly processed sets of red and infrared signals have a linear relationship therebetween.

The processing has several steps. First, the received red and infrared signals are collected from the probe detector and pre-processed. This pre-processing includes removal of ambient light and prefiltering to remove noise. The prefiltering can be a combination of linear filtering to remove unwanted additive noise and non-linear filtering to remove noise spikes. The filtered red and infrared signals consist of both a small magnitude pulsatile component which carries information about the oxygen saturation of the hemoglobin, and a plurality of large magnitude non-pulsatile components. The filtered signals are mathematically processed using either derivatives or logarithms. The results of the mathematical processing are a set of red values which are directly proportional to the red optical Extinction, and a set of infrared values which are directly proportional to the infrared optical Extinction. The red and infrared signals travel through the same pulsatile path when the data is good, which leads to a technique for both identifying good data and extracting the ratio of red optical absorption to the infrared optical absorption for that set of data measurements.

The oxygen saturation is essentially constant for a set of measurements taken over a short interval of time; e.g. less than a second. This implies that, when the data is good and the optical paths are the same for the red and infrared signals, the ratio of the mathematically processed red signal to the mathematically processed infrared signal is also a constant, except for residual noise. Consequently, for good data, a plot of the simplified infrared data points versus the simplified red data points yields points that are tightly scattered around a straight line. A "best-fit" straight line can be computed for these data points using standard mathematical techniques such as linear regression. The slope of that best-fit-line is proportional to the RRatio, which is defined as the ratio of red optical absorption to the infrared optical absorption for that data set. The RRatio carries the desired information about oxygen saturation of hemoglobin in the arterial blood.

The processed signals also contain additional information. If the plotted points are widely scattered about the best-fit-line, the excessive scatter indicates that there is excessive noise or probe artifacts in the received signals. This can be an indication the probe has fallen off the patient and/or there is patient motion. The degree of scatter of the points can be measured using standard mathematical techniques, such as the linear correlation coefficient. The measure of the scatter of the plotted points provides a quality measure of the data sample. Other statistical techniques could also be used to check the linearity of the data; for example, higher-order moments or higher-order fits. Still another test of data quality can be the intercept of the best-fit-line. The intercept is very close to zero for good data. The computed error measures can be compared to a failure threshold, possibly over a series of measurements. If there is too much error, then an alarm can be generated for the user.

The minimum size of the measured data set required for high confidence SpO2 calculations is small and therefore permits faster response of the pulse oximeter to changing values of the SpO2. It is not necessary to wait a pulse period to acquire enough samples, and high confidence values can be computed in less than a second.

DETAILED DESCRIPTION

Figure 1:
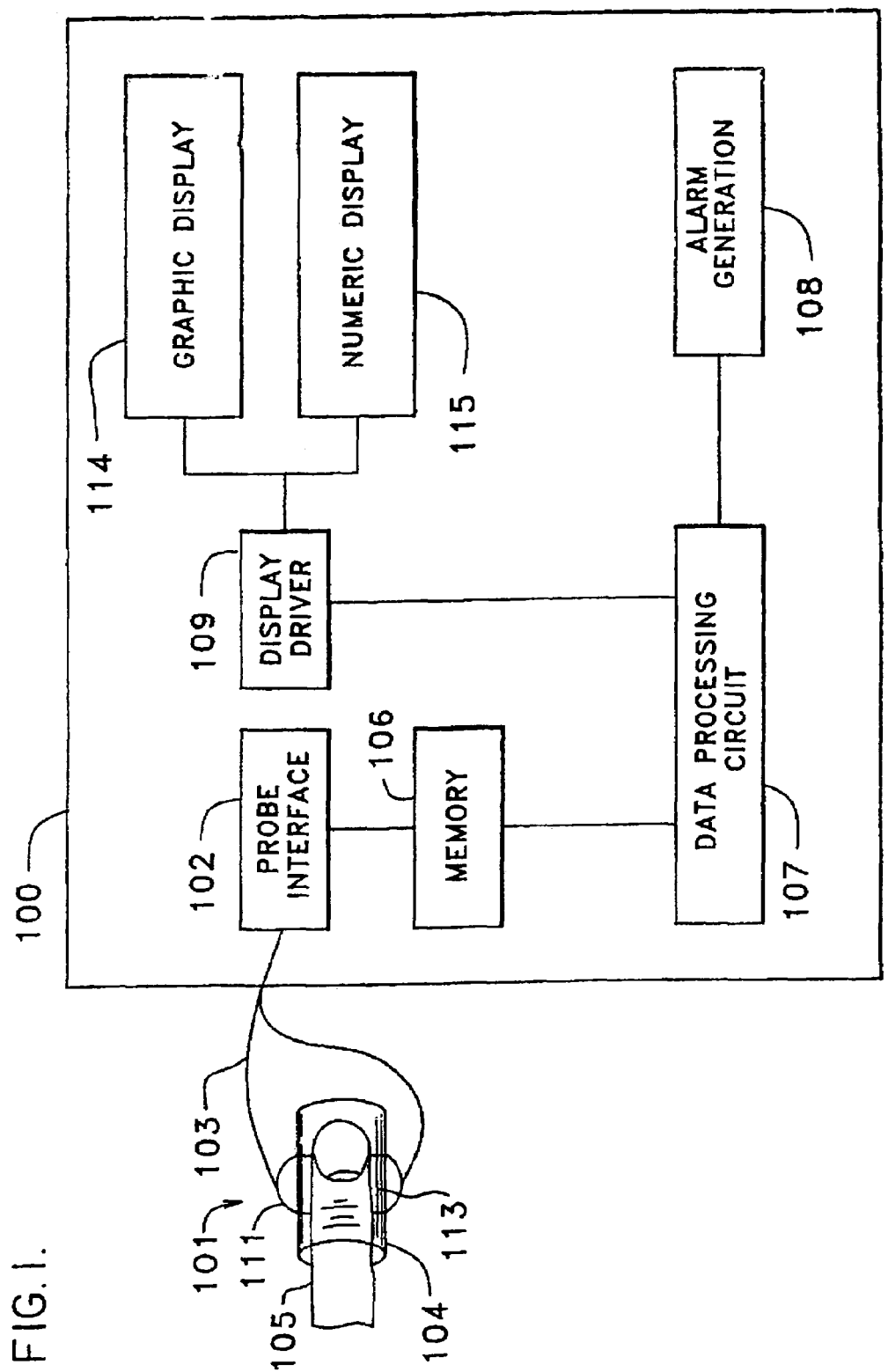
FIG. 1 illustrates in block diagram form the overall architecture of the improved system for SpO2 calculation.

This pulse oximeter system takes advantage of the basic statistical property of pulse oximetry signals that the measured blood oxygen saturation appears as a constant over a small set of measurements. Properly processed sets of red and infrared signals should have a linear relationship therebetween. Preprocessing of the sets of red and infrared signals received from the probe removes ambient light components and linear and non-linear prefiltering also removes noise to provide more accurate measurement data.

The filtered signals are mathematically processed using either derivatives or logarithms. The results of the mathematical processing are a set of red values which are directly proportional to the red optical absorption, and a set of infrared values which are directly proportional to the infrared optical absorption. The presence of good data is indicated by a linear relationship between the mathematically processed red values and the mathematically processed infrared values.

There are several types of appropriate mathematical processing. For example, one method is based on a derivative technique which finds the numerical difference between two successive red measurements. This difference results in a red term that is proportional to the product of the red optical absorption and the pulsatile path, provided that the sample rate is rapid enough for the time between measurements to be very small. Taking a similar difference between two successive infrared measurements provides an infrared term that is proportional to the product of the infrared optical absorption and the pulsatile path. For good data, the pulsatile path components are identical for both red and infrared signals, so that the ratio of the differentiated red and infrared terms cancels out the path length. The effects of different tissue thicknesses and skin pigmentation are removed by normalizing the processed signal by removing the terms that are proportional to the red and infrared non-pulsatile incident intensities.

An alternate method of mathematical processing is to use logarithms instead of derivatives. In this approach, the logarithms of the ratio of two successive red measurements are taken, which is equivalent to finding the difference between the logarithms of two successive red measurements. The same process is applied to the infrared signals. Then the ratio of the logarithmic differences of the red and infrared signals yields a term that is a function of the red and infrared absorptions and is independent of path length. This technique directly compensates for the variations in thickness of different tissues and skin pigmentation.

Regardless of whether the derivatives or logarithms are used for mathematical processing, the linearity of the mathematically processed red and infrared signals allows the use of statistical techniques such as linear regression and linear correlation to fit a straight line to the set of pairs of processed red and infrared data points and to measure the goodness of that fit. One result of this analysis is a linear regression slope and intercept and the other result is a goodness-of-fit correlation coefficient. The linear regression slope is a measure of the best fit straight line to the ratio of the red absorption coefficient and infrared absorption coefficient. This ratio is called a best-fit RRatio. This best-fit RRatio is then used in an empirical calibration formula to compute the best-fit SpO2 value. The minimum size of the data set required for high confidence SpO2 calculations is relatively small, and permits faster response of the pulse oximeter system to changing values of SpO2. It is not necessary to have a full pulse period, and responses under one second are feasible.

The goodness-of-fit correlation coefficient is a measure of linearity between the mathematically processed red and infrared signals. If the correlation coefficient is low, then the data is a poor fit. This can indicate that there is a probe-off condition or patient motion. By tracking a short history of computed correlation coefficients against predetermined failure thresholds, error conditions can be detected and appropriate alarms generated for the user. A large magnitude of the computed intercept of the best-fit-line also indicates bad data.

System Architecture

FIG. 1 illustrates in block diagram form the overall architecture of a typical pulse oximeter system including the apparatus of the present invention. The pulse oximeter system 100 consists of a probe 101 connected to probe interface circuit 102 by means of a set of electrical conductors 103. The probe 101 consists of an exterior housing 104 that applies the active elements of the probe to the tissue under test, such as a finger 105, containing an arterial blood flow that is to be monitored. Included within housing 104 is a pair of light emitting diodes 111, 112 and at least one corresponding light detector 113. The light emitting diodes 111, 112 each produce an output light beam of predetermined wavelength which is directed at the tissue under test 105 enclosed by housing 104. The light detector 113 monitors the level of light that is transmitted through or reflected from the vascularized tissue 105. In order to distinguish between the light beam produced by the red 111 and infrared 112 light emitting diodes, these light emitting diodes 111, 112 are synchronously sampled. Ambient light is measured in housing 104 by light detector 113 making measurements when the light emitting diodes 111, 112 are off.

The signals received by probe interface circuit 102 from light detector 113 are analog signals and are typically processed by additional analog circuitry and then converted by an analog-to-digital converter circuit into sets of digital measurements which are stored in memory 106. Data processing circuit 107 mathematically processes the digitized measurements stored in memory 106 to compute the oxygenation level of the hemoglobin in the arterial blood in tissue 105. It is also possible that analog circuitry can be used to perform some of the mathematical operations described herein as performed by data processing circuit 107, such as taking derivatives or logarithms.

The data processing circuit 107 also computes the pulse rate, and a pulsitility index. The results of the oxygen saturation computation and pulse rate are displayed numerically (115) via display driver 109 and the associated display 114, 115 while the plethysmographic waveform is typically displayed graphically via display 114. The pulsitility index can be done with numerical or graphical methods. In addition, data processing circuit 107 detects anomalies in the input data stored in memory 106 and "sets error codes which may be used to" activate an alarm generation circuit 108 to produce an audible and/or visual alarm to a user to indicate a data error condition. The operation of data processing circuit 107 is disclosed in additional detail below and, for the purpose of this disclosure, it is assumed that the other elements disclosed in FIG. 1 are the conventional components found in existing pulse oximeter systems.

Signal Components

Figure 8:
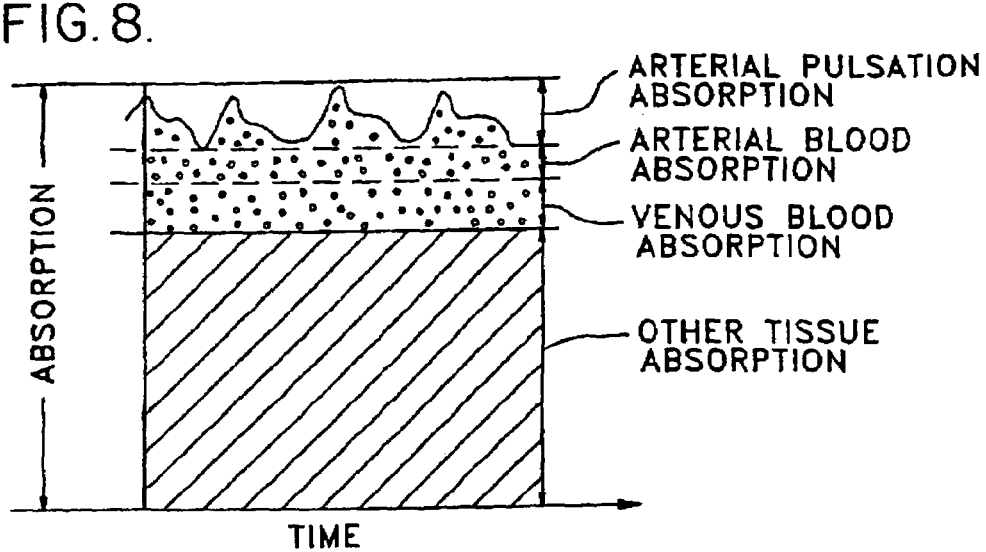
FIG. 8 illustrates in graphical form the various components of the input signal from the probe.

FIG. 8 illustrates in graphical form (not to scale) the various components of the signal produced by the light detector 113 as a result of a light beam interacting with vascularized tissue 105. The light detector output signal consists of a large magnitude non-pulsatile component and a small magnitude pulsatile component. The non-pulsatile component represents light remaining after absorption due to a combination of venous blood flow, tissue, bone, and constant arterial blood flow while the small pulsatile component is caused by the light absorption due to pulsatile arterial blood flow that is to be measured. Since the light emitting diodes 111, 112 are sampled in rapid succession, the data signals produced by the light detector 113 and transmitted to the probe interface 102 consist of a series of data points which are digitized and stored in memory 106. Since the red 111 and infrared 112 light emitting diodes are sampled in rapid succession, the digitized data points produced consist of a plurality of sets of measurements, with one set corresponding to samples of the red intensity, the other set corresponding to samples of the infrared intensity, and a third set corresponding to ambient light.

Ideally, the ratio of the normalized derivative (or logarithm) of the red intensity to the normalized derivative (or logarithm) of the infrared intensity is a constant. This constant is indicative of the partial oxygenation of the hemoglobin in the arterial blood flow. It is obvious that this ratio changes as SpO2 changes but, for a short interval with rapid enough sampling rate, the ratio remains constant.

As noted above, the actual data received by the probe interface circuit 102 can include a fairly significant noise component which is caused by a number of sources including motion of the finger 105, the introduction of ambient light into the housing 101, and various sources of electrical noise. These noise components skew the values of either or both of the magnitudes measured in each set of data points destroying the correct relationship between the red and infrared signals. Existing pulse oximeter circuits make use of various filtering techniques to minimize the impact of the noise on the SpO2 value measured by the system. However, a severe limitation of existing filtering circuits is that very little indication is provided to the user of the severity of the noise introduced into the measurements. The accuracy of the readings produced by a typical pulse oximeter system can be severely compromised by the probe 101 being improperly affixed to the patient's finger 105 without the user being able to detect this condition. In addition, only a single pass filtering technique is typically used to remove only the most egregious instances of noise in the system. The apparatus of the present invention overcomes the limitations of existing pulse oximeter systems by processing the received data in a manner that detects excessive noise introduction in the system and provides improved noise rejection in determining the SpO2 measured by probe 101.

Mathematical Background

In this system, the key parameter is called the RRatio. This parameter measures the ratio of the normalized derivative (or logarithm) of red intensity to the normalized derivative (or logarithm) of infrared intensity. For good data, this parameter corresponds to the ratio of the red arterial optical absorption to the infrared, arterial optical absorption. The significance is the RRatio can be understood by examining the optical behavior of light as it passes through tissue. The light is scattered and absorbed by all the tissues, but the light passing through a pulsing artery or arterial bed will see a moving path length. The other tissues are unmoving and contribute to the steady non-pulsatile signal, but not to the time-varying pulsatile signals. The absorption of light by arterial blood is assumed to be only a function of the oxygenation state of the hemoglobin. Other basic assumptions are that the red and infrared light travels along essentially the same optical path, and that all the hardware circuits do not introduce any bias into the signal extraction.

The waveform of the optical signal is determined by changes in the pulse length, $L_p$, and the basic optical signal is described by an exponential relationship according to Beer's law. This means that the intensity of red, $I_{Red}$, and the intensity of the InfraRed, $I_{IR}$, light absorbed by the blood in a pulsing capillary bed can be described by the following equations:

$$I_{Red} = Ambient + I_{NPRED} * Exp[-E_{Red} * C * L_p] \quad (1)$$

$$I_{IR} = Ambient + I_{NPIR} * Exp[-E_{IR} * C * L_p] \quad (2)$$

where the Red or IR optical absorption is given by the product of the Red Extinction Coefficient, $E_{Red}$, or InfraRed Extinction Coefficient, $E_{IR}$, and the hemoglobin concentrations, C. The concentration, C, and pulsatile path length, $L_p$, are the same for the red and infrared light. $I_{NPRED}$ is the non-pulsatile red intensity of the signal and is proportional to the product of the light emitting diodes intensity with attenuation factors from propagation through non-pulsatile media and sensitivity and gain factors from the detection electronics. $I_{NPIR}$ is the corresponding non-pulsatile infrared intensity.

The pulsatile exponential function puts an amplitude modulation on the non-pulsatile intensity. The equation for the non-pulsatile intensity $I_{NP}$, has several terms.

$$I_{NP} = Io * A * Exp[-\Sigma E(Ex * Cx * Lx)] \quad (3)$$

The term Io is the incident intensity. A is a composite scale factor caused by scattering losses, losses in detection, and gain in detection circuits. There is a composite exponential absorption as the light propagates through non-pulsatile intervening tissue, which can be described by a summation of the absorptions by each intervening tissue zone.

The objective of the following mathematical manipulation is to obtain the ratio of the Extinction coefficients of the Red, $E_{Red}$, and the InfraRed, $E_{IR}$, signals. This ratio is used with a calibration equation to determine how well the blood is oxygenated. It is assumed that the ambient light is perfectly subtracted from the received signals.

It is necessary to compute the Extinction coefficients from the exponentials. This can be done with the use of either logarithms or derivatives. The preferred method disclosed herein uses derivatives. If the samples are closely spaced relative to the changes in pulsatile path length, $L_p$, then a series expansion of the exponential function can be used. This means that the exponential really looks like a constant plus a term that is linearly proportional to the path length. In other words, only the first two terms of the binomial expansion need to be retained. Assume that the difference between two closely spaced in time non-pulsatile intensities is zero. Taking samples at time $t^2$ and time t1, the derivative of the red intensity can be approximated as the difference between the two samples:

$$DRed = I_{NPRED} * (Exp[-E_{Red} * C * L_p(t2x)] - Exp[-E_{Red} * C * L_p(t1)]) \approx I_{NPRED} * ([1 - E_{Red} * C * L_p(t_2)] - [1 - E_{Red} * C * L_p(t_1)]) = I_{NPRED} * (E_{Red} * C * [L_p(t_2) - L_p(t_1)]) \quad (4)$$

In equation 4 $L_p(t2)$ is the pulsatile path length at time 2 and $L_p(t1)$ is the pulsatile path length at time 1.

The derivative of the infrared intensity can be approximated in a similar manner.

$$DIR = I_{NPIR} * (EXP[-E_{IR} * C * L_p(t2)] - Exp[-E_{IR} * C * L_p(t1)]) \approx I_{NPIR} * ([1 - E_{IR} * C * L_p(t2)] - [1 - E_{IR} * C * L_p(t1)]) = I_{NPIR} * (E_{IR} * C * [L_p(t2) - L_p(t1)]) \quad (5)$$

Note that both DRed and DIR are directly proportional to the Extinction coefficients as long as $I_{NPRED}$ and $I_{NPIR}$ are constant over that sampling interval. Note also that the term $C [L_p(t2) - L_p(t1)]$ is common to both DRed and DIR. This means that the ratio of DRed and DIR is independent of the concentration and path length changes.

$$DRed/DIR = (I_{NPRED}/I_{NPIR}) * (E_{Red}/E_{IR}) \quad (6)$$

NOW the factor which is due to the ratio of received non-pulsatile intensities can be removed in several ways. In one method, analog hardware is used to separate the received intensities, by finding the low-pass DC values of the Red and Infrared.

$$(I_{NPRED}/I_{NPIR}) = (I_{NPRED\,DC}/I_{NPIRDC}) \quad (7)$$

In the preferred method, the sum of the two or more time samples is used $$I_{NPRED} = I_{NPRED(t2)} + I_{NPRED(t1)} \quad (8)$$

$$I_{NPIR} = I_{NPIR(t2)} = I_{NPIR(t1)} \quad (9)$$

An instantaneous RRatio is found by multiplying the ratio of derivatives to the ratio of the incident intensities.

instantaneous $RRatio = DRed/DIR * (I_{NPIR}/I_{NPRED}) = (E_{Red}/E_{IR}) \quad (10)$ Key Equations The instantaneous RRatio is a number computed from only two measurement pairs of red and infrared values, which can be corrupted by noise. There is another way to computed an RRatio that forms a best-fit to a larger number of measurements pairs and reduces the sensitivity to noise. Note once again that the Extinction Coefficients and incident intensities are nearly constant provided that the sample rate is fast compared to any physiological changes. This means that valid data must obey the equation of a straight line. Consequently for a small set of closely spaced samples, it must be true that:

$$DRed * I_{NPIR} = SlopeA * (DIR * I_{NPRED}) + noise, \text{ and} \quad (11)$$

where $$SlopeA = E_{Red}/E_{IR} \quad (12)$$

An alternate way to express the linear relationship may be more applicable in some cases.

$$DRed = SlopeB * DIR + noise, \text{ and} \quad (13)$$

where $$SlopeB = (I_{NPRED}/I_{NPIR}) * (E_{Red}/E_{IR}) \quad (14)$$

Equations 11 and 12 state that each value of DIR should be scaled by multiplying by $I_{NPIR}$ and that each value of DRed should be scaled by multiplying by $I_{NPRED}$. Then a linear regression of all the scaled points in the set yields a line whose slope is the best fit to the ratio of the Red Extinction to the Infrared Extinction which is the desired RRatio.

best-fit $RRatio = SlopeA$ (15)

If the incident intensities are constant over the data set, then it is not necessary to scale each value before doing the linear regression. That case corresponds to Equations 13 and 14, which indicate that the linear regression slope can be computed on DIR and DRed and then normalized by the ratio of the incident intensities.

best-fit $RRatio = SlopeB/(I_{NPRED}/I_{NPIR})$ (16)

After finding the best-fit RRatio, the SpO2 is computed from an empirical calibration formula.

Equations 11 to 16 are the key equations. They state that there is a linear relationship between the DIR and DRed provided that the data is good. Consequently, the slope of the linear regression fit to a set of data samples yields a best-fit estimate for the ratio of the Extinction Coefficients, RRatio.

The goodness of the fit can then be used as a test for checking the quality of the data. Any deviation from the linearity relationship indicates a reduced quality of the data.

For completeness, we show how the linear regression method can be used when the red and infrared signals are processed with logarithms instead of derivatives. In this case, define the difference between the logarithms of two subsequent red and infrared measurements.

$$DLogRed = (log[I_{NPRed}(t2)] - Log[I_{NPRED}(t1)]) + E_{Red} * C (L_{p(t2)} - L_{p(t1)}) \quad (17)$$

and $$DLogIR = (log[I_{NPIR}(t2)] - Log[I_{NPIR}(t1)]) + E_{IR} * C * (L_{p(t2)} - L_{p(t1)}) \quad (18)$$

If two samples are closely spaced in time, the difference between two non-pulsatile intensities goes to zero. Then:

$$DLogRed/DLogIR = E_{Red}/E_{IR} \quad (19)$$

Since the Extinctions are constant, this means that:

$$DLogIR = SlopeA * DLogRed + noise \quad (20)$$

where $$SlopeA = E_{Red}/E_{IR} \quad (12)$$

Equation 20 and Equation 11 have the same linear form. The results from equation 20 and 11 differ only if there are significant variations in incident intensity or large amounts of additive noise, or the sample spacing is too large for the series expansion to be valid.

System Implementation

Figure 2:
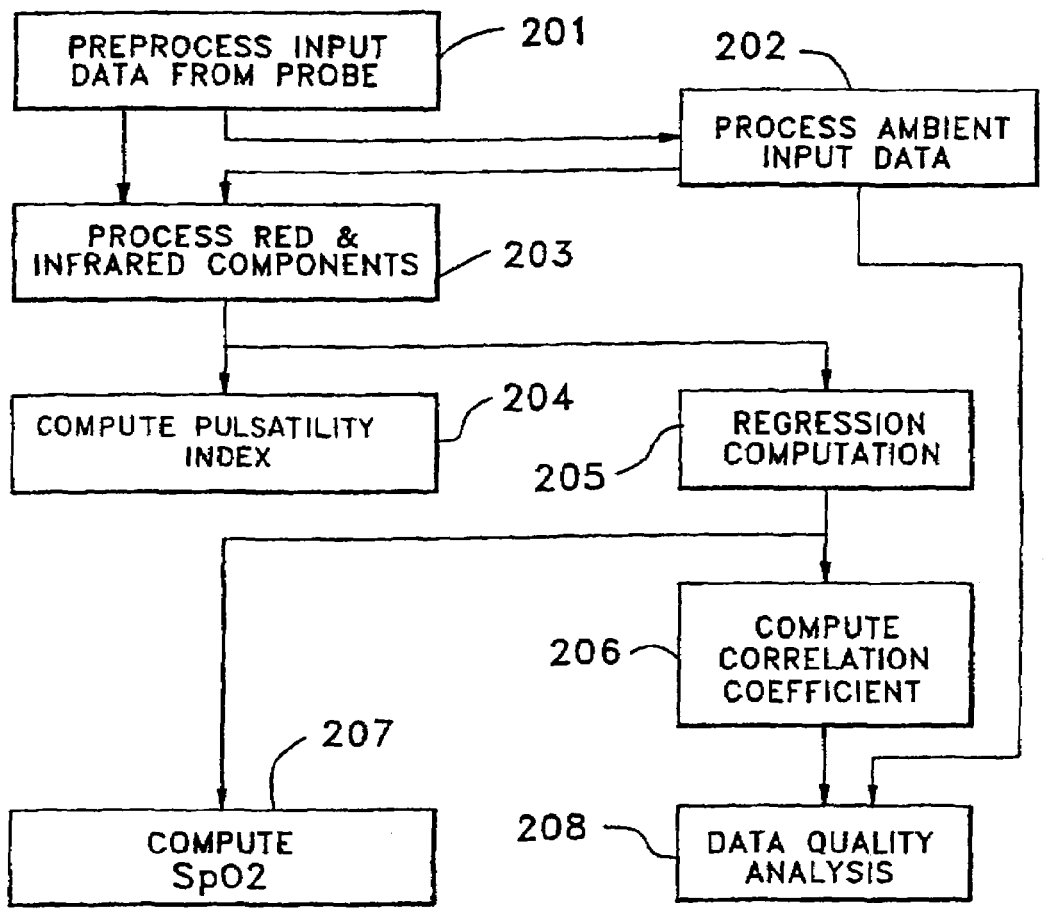
FIG. 2 illustrates in block diagram form the functional elements used by this system to perform the calculations.
Figure 3:
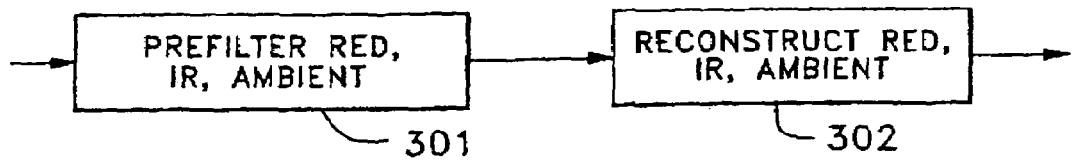
FIGS. 3–7 illustrate additional details of the various processes used in the improved system for SpO2 calculation.

FIG. 2 illustrates in block diagram form the various components used within the data processing circuit 107 of the pulse oximetry system of the present invention in order to provide improved data filtering and data acquisition. The analog data signals received from probe 101 are filtered by analog hardware and digitized by an analog to digital converter in probe interface 102 prior to application to preprocess input data from probe circuit 201. The preprocessing circuit 201 includes prefilter circuit 301 (FIG. 3) which uses digital filtering techniques for noise removal, frequency selection and data rate control. Nonlinear digital filters can be used in the prefilter circuit 301 of preprocessing circuit 201 to reduce the influence of input data that are statistically beyond the range of the other data values acquired by probe 101. These nonlinear digital filters can be implemented for example by median filters, trimmed mean filters and morphological filters.

The input data from probe 101 is typically decomposed into its non-pulsatile and pulsatile sub-elements in probe interface 102 in order to provide accurate measurements of these components. The pulsatile component typically represents 0.5% of the total input signal and the decomposition of the input signal into pulsatile and non-pulsatile components permits accurate analog to digital conversion of each of these components. Therefore, once these two sets of components have been filtered by the prefilter circuit 301 of preprocessing circuit 201, they are applied to reconstruct red, IR, and ambient circuit 302 where the components are used to return the acquired input signal back to its original form. The reconstructed infrared and red data signals are in digital form and the signal reconstructed within reconstruction circuit 302 is used for pulse computations and display 115. The red and/or infrared signals are further processed for waveform display 114 on the pulse oximeter system.

Figure 4:
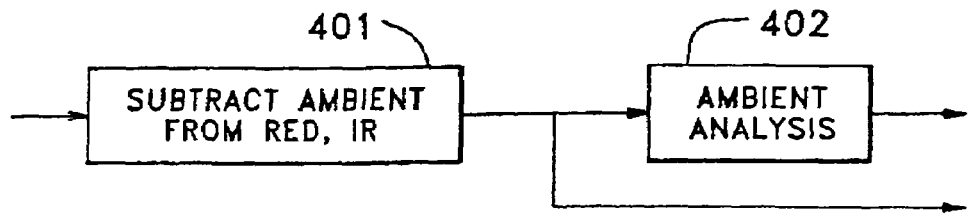

For some hardware configurations, the reconstructed red and infrared signals are transmitted to process ambient input data circuit 202 which is comprised of the elements illustrated in FIG. 4. The ambient signal is removed from the red and infrared signals in subtract ambient circuit 401. In other hardware configurations, the ambient light is removed from the red and infrared signals prior to the analog-to-digital converter. In those configurations, the preprocessed input data can be directly sent to process red and infrared component circuit 203. The resultant signal is then transmitted to process red and infrared component circuit 203. The measured ambient components are also transmitted to ambient analysis circuit 402 where the characteristics of the ambient signal are used to help determine whether there is a probe off condition or excessive noise in the input signal. This ambient analysis is forwarded to data quality analysis circuit 208 which performs the error determination function for the pulse oximeter circuit to identify any aberrant conditions in the input signals which question the validity of the measurements taken as described below.

Figure 5:
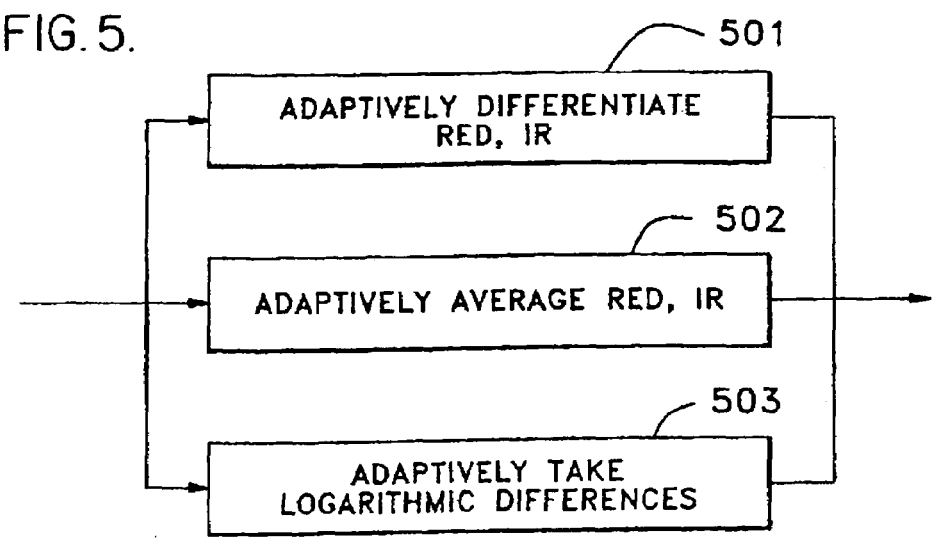

The red and infrared pulsatile components with ambient removed are applied to process red and infrared component circuit 203. The processing of the red and infrared components consists of several possible implementations illustrated in FIG. 5. One implementation adaptively differentiates 501 the red and infrared signals to perform a digital differentiation of these two signals to de-exponentiate the pulsatile component. Adaptive averaging circuit 502 performs a local average of the red and infrared signals to estimate the non-pulsatile component.

Alternatively, the differentiation can be replaced by logarithmic difference circuit 503 which performs a digital subtraction of the logarithms of two sequential red signals and the same for two sequential infrared signals. The logarithmic differences are used in place of the differential and local average values computed by circuits 501 and 502 respectively.

As a result of these computations, a plurality of sets of processed red and infrared data values are stored in memory of data processing circuit 107 wherein each set consists of the processed red and infrared data values computed at two successive sampling intervals. Successive sets of data values therefore represent successive processed samples of measurements taken in successive time intervals.

Whichever ones of these processes are selected, the output processed signals are applied to compute "pulsatility index" circuit 204 which computes a "pulsatility index" indicative of the perfusion of the hemoglobin using a weighted combination of the red and infrared processed values. The perfusion is a term used to indicate the volume of arterial blood flow for a given volume of tissue and by looking at the red and infrared signals separately, an estimation of the present blood volume change in the tissue can be determined. The "pulsatility index" is therefore only a figure that can be correlated to the true perfusion of the tissue.

Figure 6:
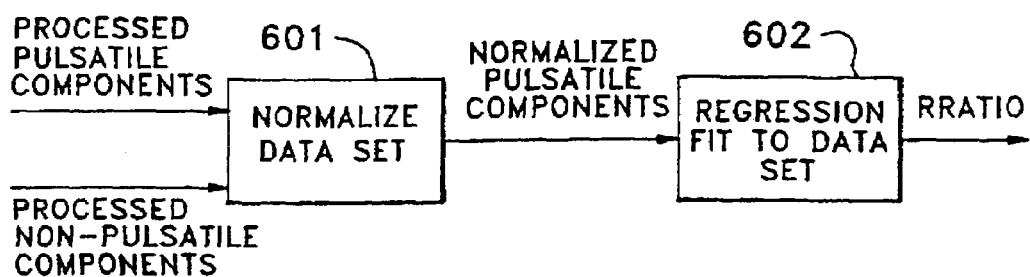
Figure 7:
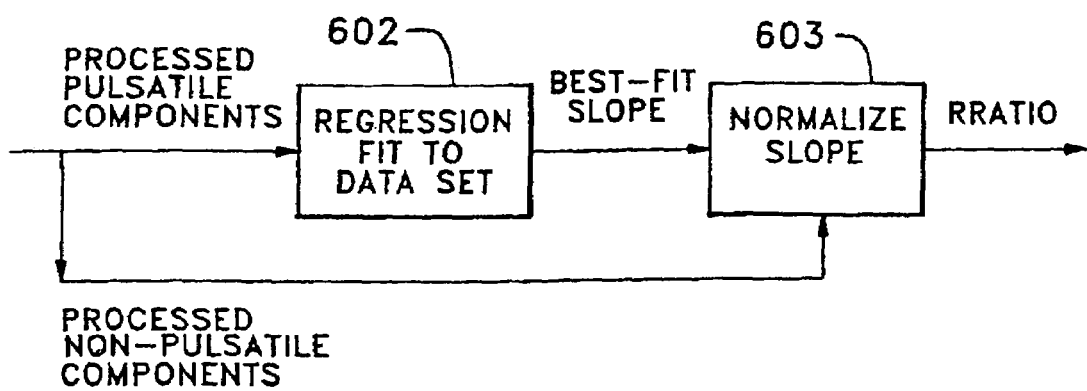
Figure 9:
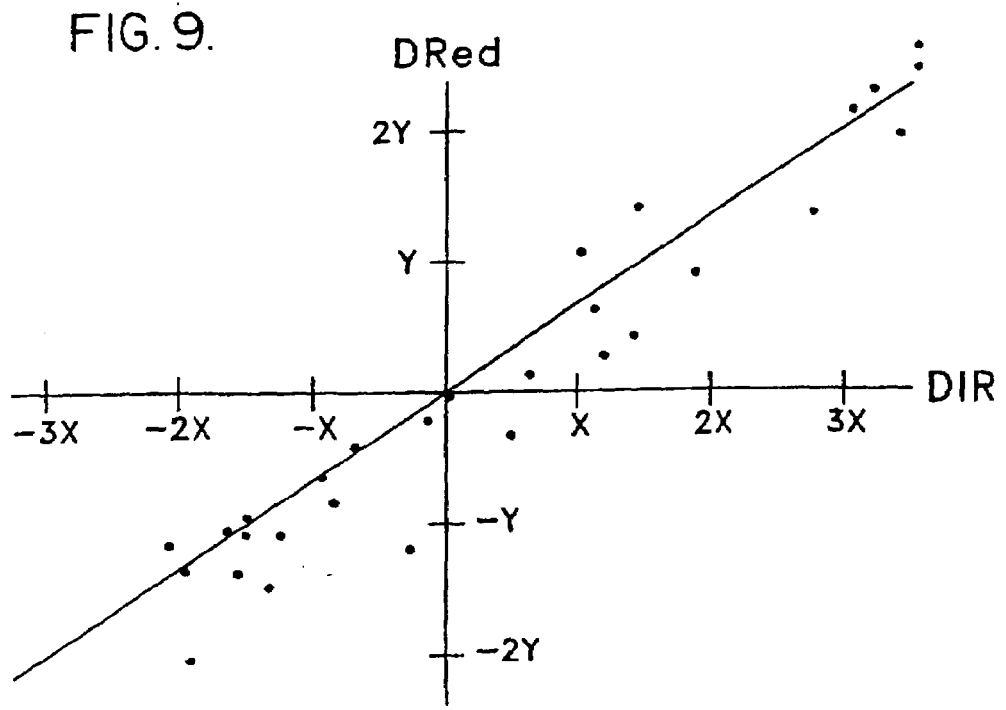
FIG. 9 illustrates in graphical form an illustrative set of data which is used in this system.

These same processed signals output by process component circuit 203 are applied to regression computation circuit 205 which is the first step used in calculating the partial oxygenation SpO2 of the hemoglobin. The regression computation circuit 205 consists at least one of the plurality of subcircuits illustrated in FIGS. 6 and 7. These circuits illustrate various combinations of regression computation and normalization. Circuit 601 is typically used to normalize the differentials received from process component circuit 203. The normalization circuit 601 multiplies each red differential by the corresponding infrared non-pulsatile intensity and multiplies each infrared differential by the corresponding red non-pulsatile intensity. The normalized differentials are then applied to regression circuit 602 which performs a linear regression fit using the normalized infrared differential as the independent variable and the normalized red differential as the dependent variable. The slope of the best fit line (FIG. 9) is a constant value that represents the best fit RRatio for that data set. A robust regression process can be implemented by removing the outliers in the collection of data points to thereby improve the least squares fit, or by other standard methods for robust linear regression.

An alternative method of processing (shown in FIG. 7) performs a regression fit to the differential values that are input to the regression computation circuit 205 and the output of the regression circuit is then normalized by normalize Slope circuit 603. In either case, the output of regression computation circuit 205 is the RRatio for the data set as well as a set of computation products that are forwarded to compute correlation coefficient circuit 206. In addition, the linear regression can be either a first order polynomial fit or a higher-order polynomial fit. In general, good input data should produce a fitted line having a finite slope, zero intercept and all higher order terms should be essentially zero.

The compute correlation circuit 206 uses the RRatio calculated by regression computation circuit 205 as well as a set of parameters used in the computation of the RRatio to determine the goodness of the linear fit of this straight line in the set of red and infrared differentials that were transmitted by process component circuit 203 to regression computation circuit 205. A correlation coefficient is calculated which represents the goodness of the linear fit of the straight line to the set of obtained data values. The intercept of the best fit line can be also computed to evaluate data quality. The correlation coefficient and zero offset values are transmitted to data quality analysis circuit 208 which uses these values as well as the ambient analyses obtained from process ambient input data circuit 202 to verify the quality of the input data.

Probe-Off Detection

A probe-off condition can be detected by measuring the goodness of the linear fit. This means that the product of the slope and its inverse should equal one if the linear fit is a good one.

There is a standard statistical technique for measuring the goodness of a linear regression fit. The Fisher Linear Correlation essentially measures the goodness of the fit by using the constraint that the slope and its inverse must be a product very close to ±1 if the fit is good. If the product of the slope and its inverse are significantly different than ±1, the data is bad. A higher order polynomial fit can be used instead of a linear and then the size of the higher order coefficients are used as a test.

Data quality analysis circuit 208 monitors the correlation coefficient as well as other indicators to identify excessive input signal noise. A neural network or knowledge-based system can be used to identify a subset of anomalies indicative of errors. These anomalies can include n successive samples that exceed a predetermined variance and/or excessive variance in the ambient signal. Furthermore, the SpO2 varies slowly as a result of physiological changes and excessive correlation of changes in the determined SpO2 with changes in the ambient is an indication of an error condition. This circuit may also receive input pulse signal data available from electrocardiograph machines which could be used to check the validity of the data and that the pulsatile rate of the data can be compared with the ECG values to identify motion artifacts in the input data. By the use of pattern matching, a feature vector can be computed to identify not only the presence of an error condition. It may also be used to classify the error.

The best fit RRatio output by regression computation circuit 205 is transmitted to compute SpO2 circuit 207 where the partial oxygenation of the hemoglobin in the arterial blood is computed using an empirical formula to identify the correspondence between the input data and the actual oxygenation value as noted above. The results of this computation are then applied to display driver 109 for numeric output on display 115. While a specific embodiment of this invention has been disclosed, it is expected that those skilled in the art can and will design alternate embodiments of this invention that fall within the scope of the appended claims.

I claim:

1. A method for use with a probe for producing a probe output potentially indicative of light absorption of arterial blood, said method comprising the steps of:

receiving said probe output from said probe and identifying a portion of said probe output for potential processing using an arterial oxygen saturation algorithm;

analyzing said portion of said probe output to obtain an indication of a quality of said output;

making a determination, based on said indication of said quality of said output, whether said output reflects a high quality signal including substantially undistorted information reflective of patient oxygen saturation or a low quality signal; and based on said determination, selectively providing either a first processor output based on said arterial oxygen saturation algorithm in the case of said high quality signal or a second processor output in the case of said low quality signal;

wherein said signal output includes first and second signals corresponding to light of first and second wavelengths, respectively received by the probe, and said step of analyzing comprises determining a degree of correlation between said first and second signals.

2. A method as set forth in claim 1, wherein said step of analyzing comprises identifying a characteristic based on said probe output deemed unlikely to correspond to patient physiology.

3. A method as set forth in claim 1, wherein said step of analyzing comprises identifying a variation in values calculated from said probe output deemed unlikely to correspond to patient physiology.

4. A method as set forth in claim 3, wherein said identified variation corresponds to an apparent abrupt change in arterial oxygen saturation.

5. A method as set forth in claim 1, wherein said obtained indication corresponds to a level of confidence that said oxygen saturation algorithm will provide an accurate result.

6. A method as set forth in claim 1, wherein said second processor output indicates a low quality signal status.

7. A method for use with a probe for producing a probe output potentially indicative of light absorption of arterial blood, said method comprising the steps of:

receiving said probe output from said probe and identifying a portion of said probe output for potential processing using an arterial oxygen saturation algorithm;

analyzing said portion of said probe output to obtain an indication of a quality of said output;

making a determination, based on said indication of said quality of said output, whether said output reflects a high quality signal including substantially undistorted information reflective of patient oxygen saturation or a low quality signal;

based on said determination, selectively providing either a first processor output based on said arterial oxygen saturation algorithm in the case of said high quality signal or a second processor output in the case of said low quality signal; and prior to providing said first processor output, selecting between separate processing paths to generate said first processor output.

8. A method as set forth in claim 7, wherein said step of analyzing comprises identifying a characteristic based on said probe output deemed unlikely to correspond to patient physiology.

9. A method as set forth in claim 7, wherein said step of analyzing comprises identifying a variation in values calculated from said probe output deemed unlikely to correspond to patient physiology.

10. A method as set forth in claim 9, wherein said identified variation corresponds to an apparent abrupt change in arterial oxygen saturation.

11. A method as set forth in claim 7, wherein said obtained indication corresponds to a level of confidence that said oxygen saturation algorithm will provide an accurate result.

12. A method as set forth in claim 7, wherein said step of selecting involves determining whether or not to provide a result based on application of said arterial oxygen saturation algorithm.

13. A pulse oximetry apparatus, comprising:
a port for receiving a probe output from an oximeter probe, said probe output providing information potentially indicative of light absorption of arterial blood; and
a processor operative for:
identifying a portion of said probe output for potential processing using an arterial oxygen saturation algorithm;
analyzing said identified portion of said probe output to obtain an indication of a quality of said output;
processing said detector signal to obtain processed information, wherein said processed information reduces an effect of an undesired signal portion on an oxygen saturation calculation; and
depending on a result of said signal quality analysis, using said processed information to provide an oxygen saturation output based on said algorithm;
wherein said probe output includes first and second signals corresponding to light of first and second wavelengths, respectively received by the probe, and said analyzing comprises determining a degree of correlation between said first and second signals.

14. An apparatus as set forth in claim 13, wherein said processor is operative to identify a characteristic based on said probe output deemed unlikely to correspond to patient physiology.

15. An apparatus as set forth in claim 13, wherein said processor is operative to identify a variation in values calculated from said probe output deemed unlikely to correspond to patient physiology.

16. An apparatus as set forth in claim 15, wherein said identified variation corresponds to an apparent abrupt change in arterial oxygen saturation.

17. An apparatus as set forth in claim 13, wherein said obtained indication corresponds to a level of confidence that said oxygen saturation algorithm will provide an accurate result.

18. An apparatus as set forth in claim 13, wherein said processor is operative for obtaining said processed information by excluding data corresponding to said undesired signal portion.

19. An apparatus as set forth in claim 18, wherein said excluded data is identified based on a time domain analysis.

20. A method for use in pulse oximetry, comprising the steps of:
receiving a detector signal from a pulse oximeter detector, wherein said detector signal includes a desired signal portion for use in determining blood oxygen saturation and an undesired signal portion;
performing a first signal quality analysis on said detector signal and comparing a signal quality thereby determined to a threshold;
processing said detector signal to obtain processed information, wherein said processed information reduces an effect of said undesired signal portion on an oxygen saturation calculation; and
depending on a result of said signal quality analysis, using said processed information to provide an oxygen saturation output.

21. A method as set forth in claim 20, wherein said undesired signal portion includes artifact and said step of processing comprises implementing an algorithm for calculating blood oxygen saturation with reduced interference due to said artifact.

22. A method as set forth in claim 21, wherein said algorithm involves excluding certain data deemed to reflect artifact.

23. A method as set forth in claim 20, wherein said signal quality analysis involves obtaining a measurement from said detector signal and comparing said measurement to a threshold to determine whether said signal is likely to yield reliable blood oxygen saturation information.

24. A method for use in pulse oximetry, comprising:
obtaining first and second detector signals corresponding to first and second optical signals of respective first and second wavelengths, wherein said first and second optical signals are attenuated by patient tissue;
using a mathematical model to distinguish certain data associated with desired signal portions from data associated with artifact within at least one of said first and second detector signals, said mathematical model reflecting a correlation relationship between said first and second detector signals;
selectively eliminating data associated with artifact to obtain a cleansed data set;
providing an output based on said cleansed data set that is substantially free of said data associated with said artifact; and
generating said mathematical model using a plurality of corresponding portions of said first and second detector signals within a time window;
wherein said generating step further comprises:
using a statistical relationship between said corresponding portions of said first and second detector signals within said time window.

25. The method of claim 24, further comprising:
performing a linear regression analysis on said corresponding data portions of said first and second detector signals to generate a best fit line for said corresponding data portions.

26. An apparatus as set forth in claim 24, wherein said step of eliminating comprises identifying said data associated with said artifact based on said mathematical model and excluding said data associated with said artifact from a calculation of a physiological parameter.

27. A method for use in pulse oximetry, comprising:
obtaining first and second detector signals corresponding to first and second optical signals of respective first and second wavelengths, wherein said first and second optical signals are attenuated by patient tissue;
using a mathematical model to distinguish certain data associated with desired signal portions from data associated with artifact within at least one of said first and second detector signals, said mathematical model reflecting a correlation relationship between said first and second detector signals;
selectively eliminating data associated with artifact to obtain a cleansed data set;
providing an output based on said cleansed data set that is substantially free of said data associated with said artifact;
wherein said using a mathematical model to distinguish step comprises performing a statistical analysis of data associated with at least one of said first and second detector signals in relation to said correlation relationship between said first and second detector signals.

28. The method of claim 27, wherein said using a mathematical model to distinguish step comprises identifying data outside a predetermined statistical threshold as said data associated with artifact.

29. An apparatus as set forth in claim 27, wherein said step of eliminating comprises identifying said data associated with said artifact based on said mathematical model and excluding said data associated with said artifact from a calculation of a physiological parameter.

30. An apparatus as set forth in claim 27, wherein said data associated with said desired signal portions is distinguished from said data associated with said artifact based on a deviation from said correlation relationship.

31. A method for use in pulse oximetry, comprising:
obtaining first and second detector signals corresponding to first and second optical signals of respective first and second wavelengths, wherein said first and second optical signals are attenuated by patient tissue;
identifying a time window including at least a portion of each of said first and second signals, wherein a signal ratio of said first and second detector output signals is assumed constant over said window;
performing a statistical analysis of a first data portion associated with at least one of said first and second detector signals within said window;
identifying a second data portion within said window as being affected by artifact;
based on said statistical analysis and said step of identifying, providing an output regarding a physiological parameter of a patient, wherein said output has enhanced tolerance with respect to artifact;
wherein said step of performing further comprises:
determining correlations between a plurality of corresponding portions of said first and second detector signals within said time window; and
generating a best fit line for said correlations wherein data associated with said best fit line corresponds to said signal ratio.

32. A method for use in pulse oximetry, comprising:
obtaining first and second detector signals corresponding to first and second optical signals of respective first and second wavelengths, wherein said first and second optical signals are attenuated by patient tissue;
identifying a time window including at least a portion of each of said first and second signals, wherein a signal ratio of said first and second detector output signals is assumed constant over said window;
performing a statistical analysis of a first data portion associated with of at least one of said first and second detector signals within said window;
identifying a second data portion within said window as being affected by artifact;
based on said statistical analysis and said step of identifying, providing an output regarding a physiological parameter of a patient, wherein said output has enhanced tolerance with respect to artifact;
wherein said step of performing a statistical analysis comprises determining a deviation of data in said data portion to said signal ratio.

33. A method for use in pulse oximetry, comprising:
obtaining first and second detector signals corresponding to first and second optical signals of respective first and second wavelengths wherein said first and second optical signals are attenuated by patient tissue;
identifying a time window including at least a portion of each of said first and second signals, wherein a signal ratio of said first and second detector output signals is assumed constant over said window;
performing a statistical analysis of a first data portion associated with at least one of said first and second detector signals within said window;
identifying a second data portion within said window as being affected by artifact;
based on said statistical analysis and said step of identifying, providing an output regarding a physiological parameter of a patient, wherein said output has enhanced tolerance with respect to artifact; and
performing an artifact elimination process that substantially eliminates said second data portion within said window.

34. An apparatus as set forth in claim 33, wherein said signal ratio is proportional to arterial oxygen saturation.

35. An apparatus as set forth in claim 33, wherein said step of identifying is based on said statistical analysis.

36. An apparatus as set forth in claim 33, wherein said step of performing comprises excluding said second data portion from a calculation of said physiological parameter.

37. An apparatus as set forth in claim 33, wherein said step of performing comprises processing said second data portion in a time domain.

38. A method for use in pulse oximetry, comprising:
obtaining first and second detector signals corresponding to first and second optical signals of respective first and second wavelengths, wherein said first and second optical signals are attenuated by patient tissue;
identifying a time window including at least a portion of each of said first and second signals, wherein a signal ratio of said first and second detector output signals is assumed constant over said window;
performing a statistical analysis of a first data portion associated with at least one of said first and second detector signals within said window;
identifying a second data portion within said window as being affected by artifact;
based on said statistical analysis and said step of identifying, providing an output regarding a physiological parameter of a patient, wherein said output has enhanced tolerance with respect to artifact;

wherein providing said output comprises providing an oxygen saturation output.

39. An apparatus as set forth in claim 38, wherein said signal ratio is proportional to arterial oxygen saturation.

40. An apparatus as set forth in claim 38, wherein said step of identifying is based on said statistical analysis.

41. An apparatus as set forth in claim 38, wherein said step of performing comprises excluding said second data portion from a calculation of said physiological parameter.

42. An apparatus as set forth in claim 38, wherein said step of performing comprises processing said second data portion in a time domain.

43. An apparatus as set forth in claim 38, wherein said statistical analysis is based on a correlation relationship between said first and second optical signals.

* * * * *